United States Patent [19]

Nishiki et al.

[11] Patent Number: 5,345,938
[45] Date of Patent: Sep. 13, 1994

[54] DIAGNOSTIC APPARATUS FOR CIRCULATORY SYSTEMS

[75] Inventors: Masayuki Nishiki; Shigemi Fujiwara, both of Ootawara; Mikihito Hayashi; Akira Tsukamoto, both of Tochigi; Kinya Takamizawa, Utsunomiya; Masayuki Takano, Ootawara; Seiichiro Nagai, Tochigi, all of Japan

[73] Assignee: Kabushiki Kaisha Toshiba, Kawasaki, Japan

[21] Appl. No.: 952,914

[22] Filed: Sep. 28, 1992

[30] Foreign Application Priority Data

Sep. 30, 1991 [JP] Japan .................................. 3-251296

[51] Int. Cl.$^5$ ............................ A61B 8/00; A61B 8/12
[52] U.S. Cl. ............................ 128/660.04; 128/662.06
[58] Field of Search ................... 128/660.01, 660.04, 128/653, 660.07, 654, 662.06

[56] References Cited

U.S. PATENT DOCUMENTS

| | | | |
|---|---|---|---|
| 4,665,925 | 5/1987 | Millas | 128/662.06 X |
| 5,065,761 | 11/1991 | Pell | 128/660.031 |
| 5,081,997 | 1/1992 | Bosley, Jr. et al. | 128/654 X |
| 5,203,337 | 4/1993 | Feldman | 128/660.01 X |

Primary Examiner—Francis Jaworski
Attorney, Agent, or Firm—Oblon, Spivak, McClelland, Maier & Neustadt

[57] ABSTRACT

A diagnostic apparatus for diagnosing the circulatory system of a patient, including an X-ray diagnostic system and an ultrasonic diagnostic system. The ultrasonic diagnostic system has an ultrasonic catheter for insertion into the circulatory systems of the patient and for scanning a circulatory organ with an ultrasonic wave to thereby an ultrasonic tomogram. A roadmap image is obtained prior to the ultrasonic diagnosis. When the ultrasonic catheter is inserted into the circulatory system of the patient, the X-ray diagnosis is performed to obtain a live image of the circulatory system which includes a picture of the catheter and is displayed overlapped on the roadmap image. The ultrasonic catheter is inserted into the circulatory system of the patient while the location of the catheter is monitored from the overlapped display of the live image and the roadmap image.

11 Claims, 12 Drawing Sheets

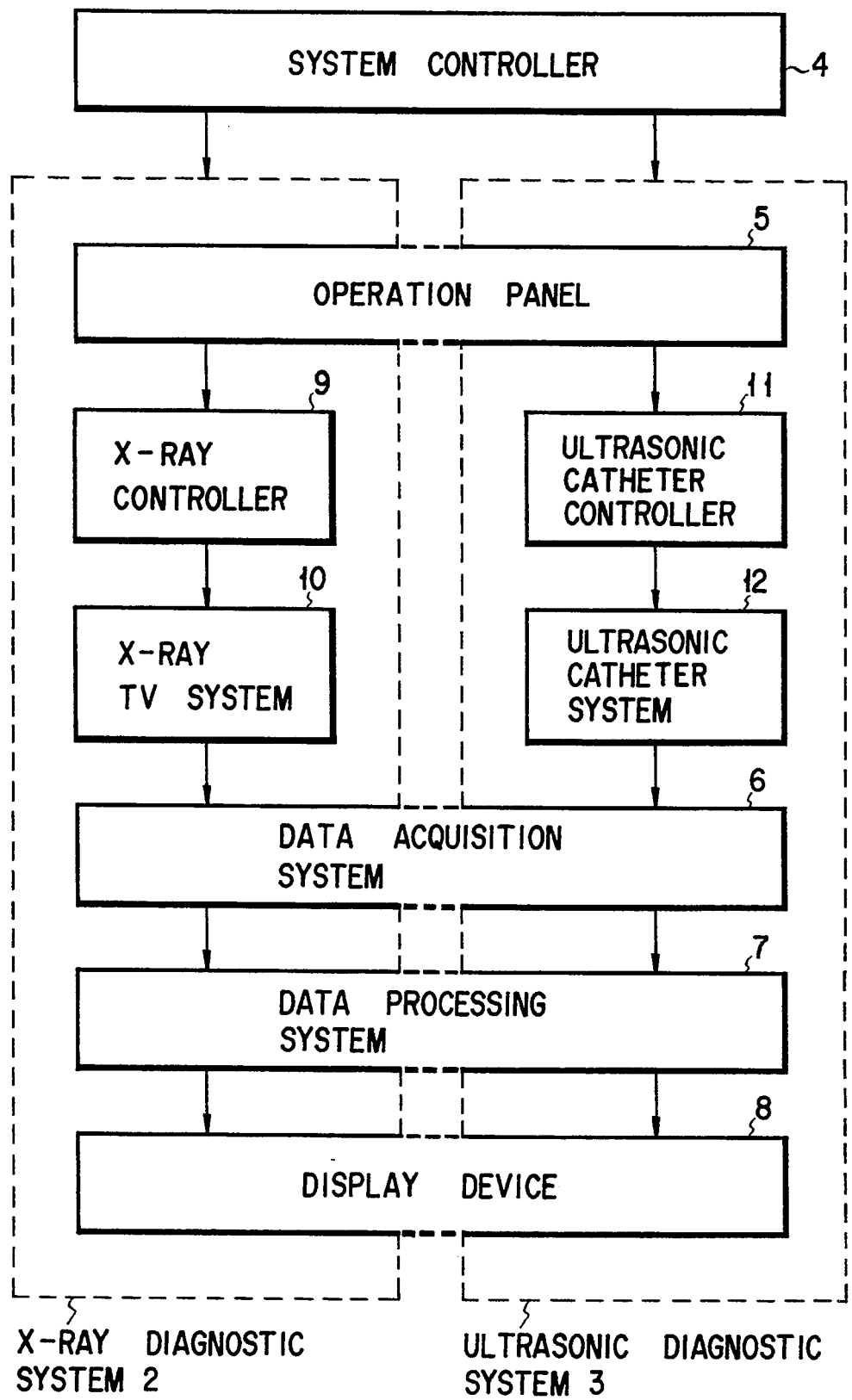
F I G. 1

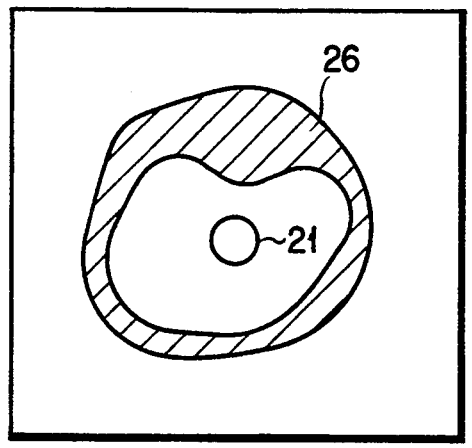
F I G. 4
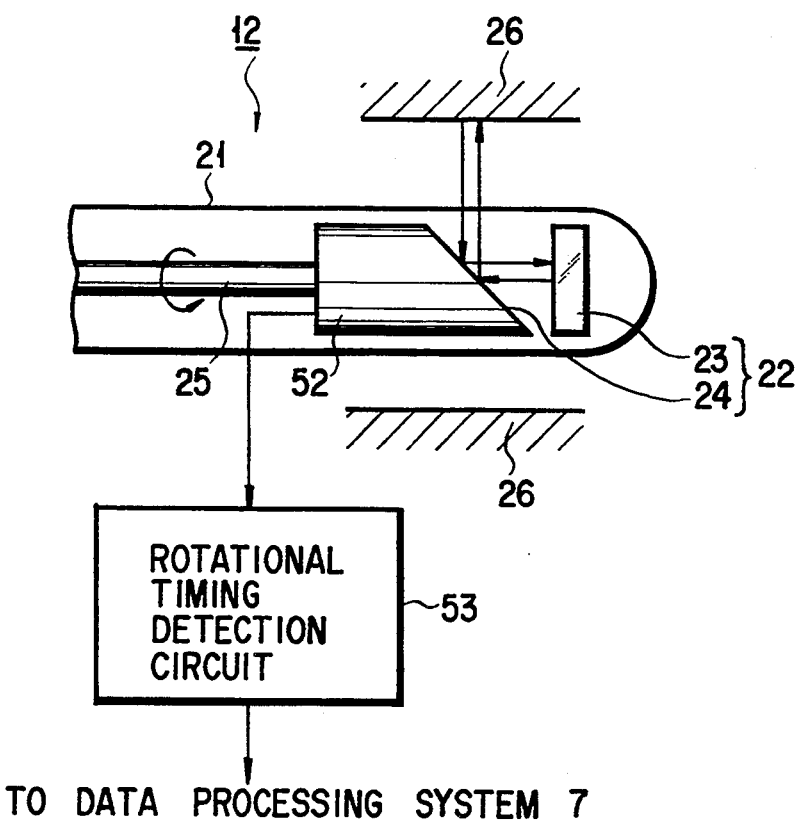
F I G. 5

$\alpha = 0°$ $\alpha = 45°$ $\alpha = 90°$ $\alpha = 135°$ $\alpha = 180°$ $\alpha = 225°$ $\alpha = 270°$ $\alpha = 315°$

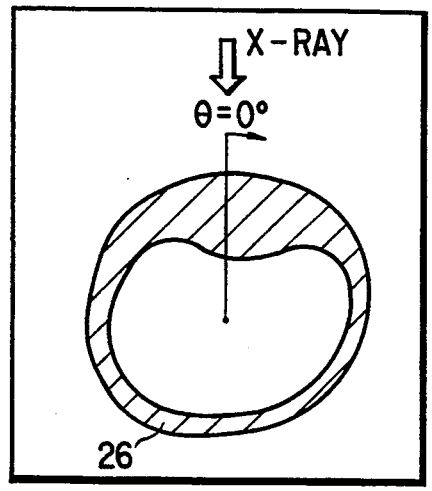
F I G. 13A
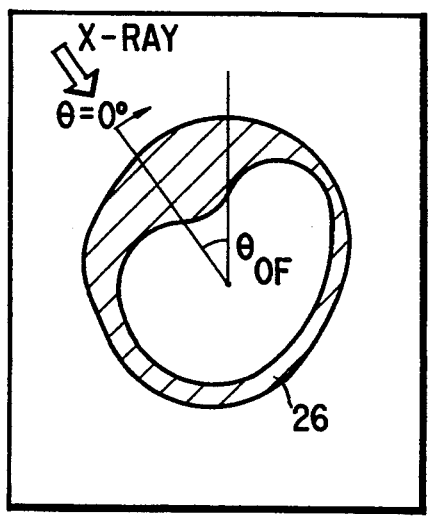
F I G. 13B
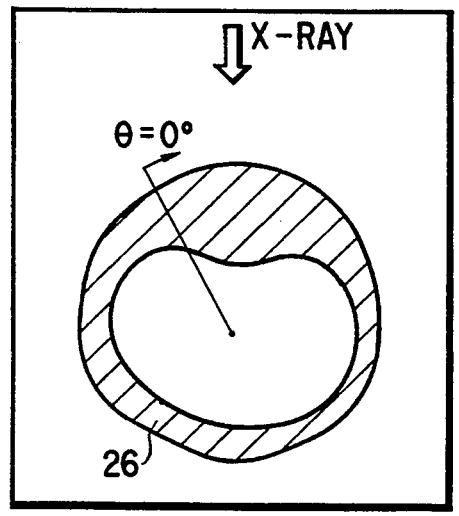
F I G. 13C

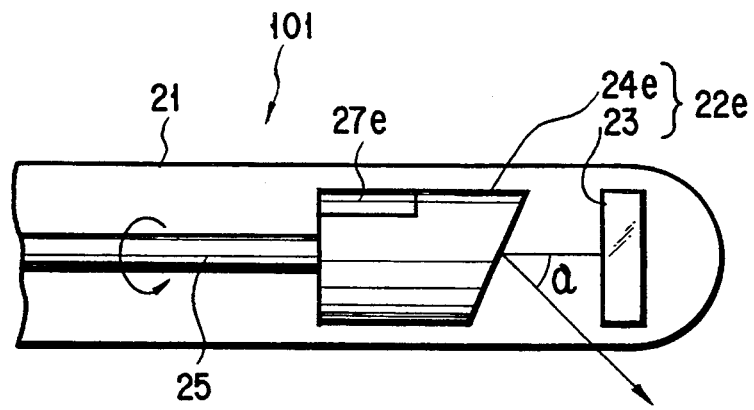
F I G. 15A
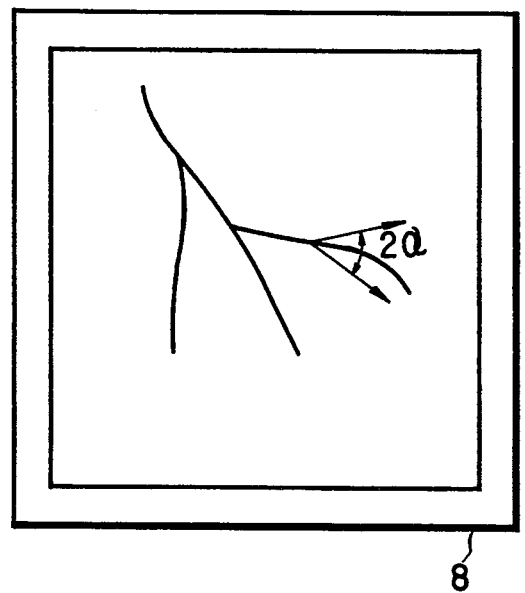
F I G. 15B

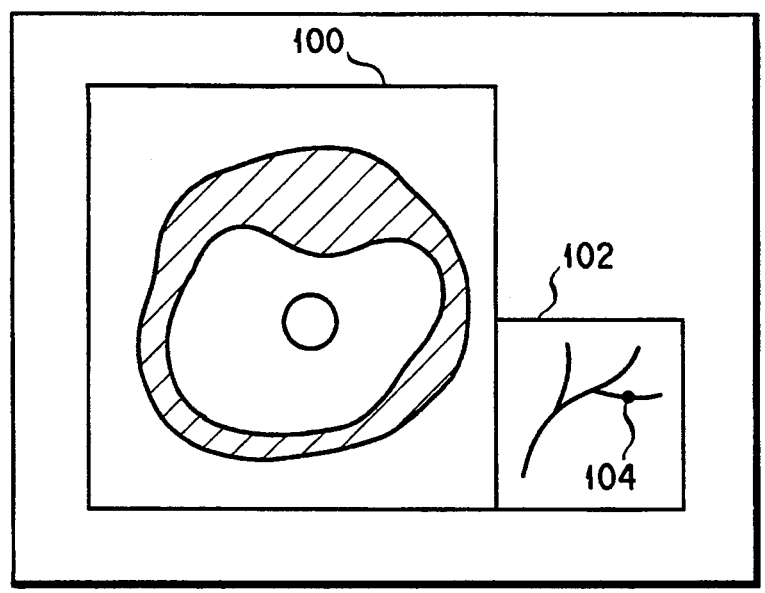
F I G. 16

DIAGNOSTIC APPARATUS FOR CIRCULATORY SYSTEMS

BACKGROUND OF THE INVENTION

1. Field of the Invention

The present invention relates to a diagnostic apparatus for circulatory systems, particularly to a diagnostic apparatus for circulatory systems having an ultrasonic tomogram function using a probe inserted into a circulatory system, and an X-ray radiograph function.

2. Description of the Related Art

In recent years, there has been developed an ultrasonic catheter apparatus for obtaining an ultrasonic tomogram by using a catheter inserted into a blood vessel. An ultrasonic transducer is provided in a distal end of the catheter and an ultrasonic wave is radially scanned so that the 360° ultrasonic tomogram of the blood vessel around the distal end of the catheter is obtained. Although this apparatus allows an operator to observe the whole cross-section of the wall of the blood vessel, it has a drawback that it is not possible to know the location of the ultrasonic tomogram in the blood vessel.

In order to know the location of the ultrasonic tomogram it is necessary to use an X-ray diagnostic apparatus together with the ultrasonic catheter apparatus. Prior to the insertion of the ultrasonic catheter, a catheter for injecting a contrast medium into the blood vessel is inserted into the blood vessel, and, by injecting the contrast medium, a roadmap image is obtained which indicates the shape of the blood vessel. Then, while the ultrasonic catheter is inserted and the ultrasonic tomogram of the blood vessel is being obtained, X-ray radiation is also performed which gives a live image of the blood vessel. This live image shows the shape of the catheter, and thereby it is possible to determine the exact position of the ultrasonic catheter by comparing the live image with the roadmap image.

However, even though the location of the distal end of the ultrasonic catheter can be determined, the orientation of the patient cannot be known from the ultrasonic tomogram. More particularly, when a stenosis of the blood vessel is found in the ultrasonic tomogram, it cannot be determined whether the stenosis is present on the heart side of the vessel or not.

Further, in order to install two apparatuses in an examination room it is necessary to have an extremely large space. In addition, simultaneous operation of the two apparatuses is quite cumbersome for handling.

These drawbacks are present not only when the ultrasonic catheter apparatus for diagnosis is used but also when an ultrasonic catheter apparatus for treatment, for example, a balloon catheter, is used.

SUMMARY OF THE INVENTION

Accordingly, it is an object of the present invention to provide a diagnostic apparatus for circulatory systems which obtains an ultrasonic tomogram of a circulatory organ and makes it possible to determine the exact location and direction of the ultrasonic tomogram with respect to the entire circulatory system and orientation of the patient.

Another object of the present invention is to provide a diagnostic apparatus for circulatory systems which has the functions of obtaining an ultrasonic tomogram and of obtaining an X-ray radiograph in combination and provides an integral control and display of two functions and of two kinds of images, thereby reducing the size of the whole apparatus and improving its performance.

A circulatory system diagnostic apparatus for circulatory systems according to the present invention comprises X-ray diagnostic means for radiating an X-ray to an object to obtain a radiograph, ultrasonic diagnostic means, inserted into the circulatory systems of the object, for scanning a circulatory organ with an ultrasonic wave to obtain an ultrasonic tomogram, control means, connected to said X-ray diagnostic means and said ultrasonic diagnostic means, for controlling said X-ray diagnostic means and said ultrasonic diagnostic means, signal processing means, connected to said X-ray diagnostic means and said ultrasonic diagnostic means, for signal-processing the radiograph and the tomogram, and display means, connected to said signal processing means, for displaying the radiograph and the ultrasonic tomogram.

Another diagnostic apparatus for circulatory systems according to the present invention comprises X-ray diagnostic means for radiating an X-ray to an object to obtain a radiograph, ultrasonic diagnostic means, inserted into the circulatory system of the object, for scanning a circulatory organ with an ultrasonic wave to obtain an ultrasonic tomogram, means for detecting an X-ray radiation direction in the ultrasonic tomogram, and display means for displaying the ultrasonic tomogram such that the detected X-ray radiation direction is maintained in a predetermined direction in the ultrasonic tomogram.

According to the diagnostic apparatus for circulatory systems of the present invention, the direction of the X-ray radiation in the ultrasonic tomogram is constant and indicated in display, and the ultrasonic tomogram and the X-ray radiograph are displayed side by side, so that the observer can always know the exact position and direction of the ultrasonic tomogram with respect to the orientation of the subject's body.

According to the diagnostic apparatus for circulatory systems of the present invention, it is possible to integrate the process of obtaining an ultrasonic tomogram and an X-ray radiograph, thereby making it possible to reduce the space necessary for apparatus installment and to improve the operability of the apparatus.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a block diagram showing a first embodiment of a diagnostic apparatus for circulatory systems according to the present invention;

FIG. 4 illustrates an ultrasonic tomogram obtained in the first embodiment;

FIG. 5 shows an ultrasonic catheter of a fourth embodiment according to the present invention;

FIGS. 13A, 13B, and 13C illustrate a change in display of the image during the correction of the $r$-$\theta$ address of the image in the fourth embodiment;

FIGS. 15A and 15B illustrate a fifth embodiment of the present invention in which a blood flow is measured; and FIG. 16 shows an example of display of the image in a sixth embodiment of the present invention.

DETAILED DESCRIPTION OF THE PREFERRED EMBODIMENTS

Figure 2:
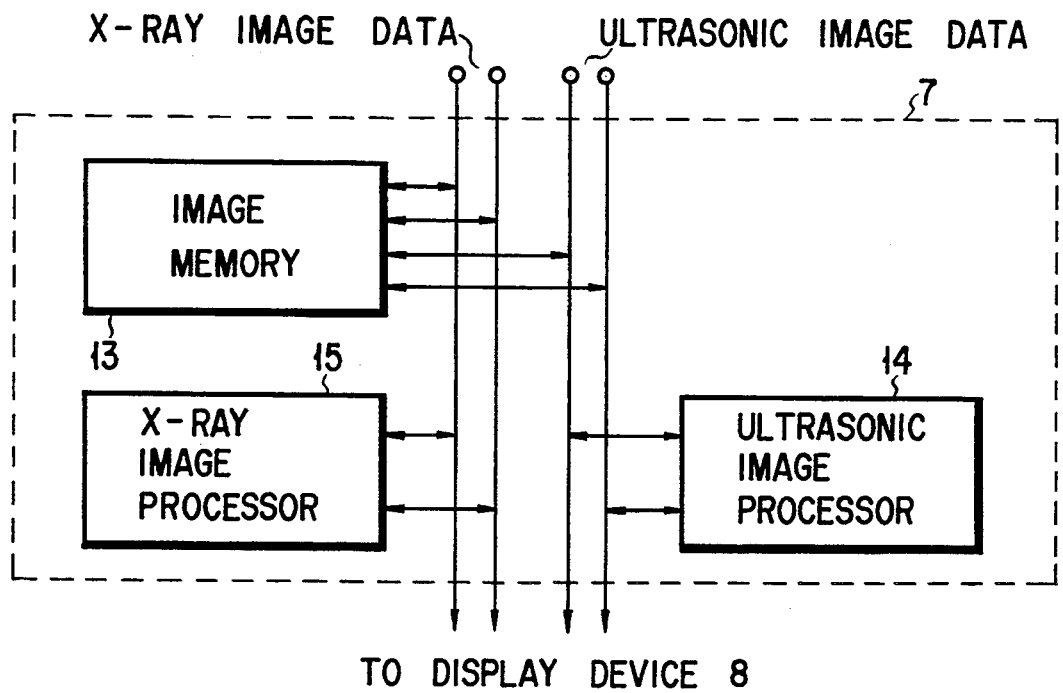
FIG. 2 is a block diagram of a data processing system of FIG. 1.

A preferred embodiment of a diagnostic apparatus for circulatory systems according to the present invention will now be described with reference to the accompanying drawings.

First Embodiment

FIG. 1 is a block diagram illustrating the structure of a first embodiment. The diagnostic apparatus of the first embodiment includes an X-ray diagnostic system 2 for obtaining an X-ray radiograph of a subject patient, an ultrasonic diagnostic system 3 for obtaining an ultrasonic tomogram of a wall of a blood vessel, and a system controller 4 for controlling these two diagnostic systems 2 and 3. The X-ray diagnostic system 2 and ultrasonic diagnostic system 3 share in common an operation panel 5, data acquisition system 6, data processing system 7, and display device 8. The operation panel 5 common to these two diagnostic systems 2 and 3 is provided in an integral manner with switches for executing radiography and those for obtaining an ultrasonic tomogram. Further, with the display device 8 common to these two diagnostic systems 2 and 3, the radiograph and the ultrasonic tomogram are displayed in one frame in a multi-window mode.

The X-ray diagnostic system 2 comprises an X-ray controller 9 which is controlled through the operation panel 5, and an X-ray TV system 10 which is controlled by the X-ray controller 9 for radiating X-rays onto the patient and for detecting X-rays being transmitted therethrough, radiograph data obtained by the X-ray TV system 10 is temporarily stored in the data acquisition system 6, and after being processed by the data processing system 7, it is displayed on the display device 8. The data processing is performed both before the data is stored in the data processing system 7 and after it is read out from the data processing system 7. Usually, the data processing is performed before the data is stored in the data processing system 7 and the processed data is also stored in the data processing system 7.

The ultrasonic diagnostic system 3 comprises an ultrasonic catheter controller 11 which is controlled through the operation panel 5, and an ultrasonic catheter system 12 which obtains an ultrasonic tomogram of a wall of the blood vessel by radially scanning an ultrasonic wave transmitted from an ultrasonic transducer in the catheter which is inserted into the blood vessel, and detecting the ultrasonic wave reflected from the wall of the blood vessel. The data of the ultrasonic tomogram obtained by the ultrasonic catheter system 12 is temporarily stored in the data acquisition system 6, and after being processed by the data processing system 7, it is displayed on the display device 8.

Though it is described that the operation panel 5, data acquisition system 6, data processing system 7, and display device 8 are provided as common both to the X-ray diagnostic system 2 and ultrasonic diagnostic system 8, or their portions commonly shared by the two diagnostic systems are integrated, this integration is not limited to physical integration of the relevant systems but it is possible to operate these portions as integral under the control of the system controller 4. For example, instead of one display capable of displaying a radiograph and ultrasonic tomogram in one frame in a multi-window mode, two displays each displaying the radiograph and ultrasonic tomogram may be used.

The data acquisition system 6 includes an A/D converter which converts analog image data into digital image data and an address converter (scan converter) for changing the scanning direction of the ultrasonic tomogram data. As an ultrasonic tomogram is expressed in terms of the $r$-$\theta$ coordinate ($r$ is a distance between the center of the radial scan and the reflection point and $\theta$ is a scanning angle), it is necessary to convert the coordinate of the ultrasonic tomogram to the X-Y coordinate.

The display device 8 includes a D/A converter for converting the digital image data from the data processing system 7 to an analog image signal to be displayed.

The block diagram of the data acquisition system 7 is shown in FIG. 2. It includes an image memory 13 for storing the radiograph data and the ultrasonic tomogram data from the data acquisition system 6, an ultrasonic image processor 14 which processes the ultrasonic image data, and an X-ray image processor 15 which processes the X-ray image data. As the image memory 13 is shared commonly by the X-ray image data and the ultrasonic image data, even when only one type of image data is present, it can effectively use the memory 13. If there are provided respective memories for the X-ray image data and the ultrasonic image data, one of the memories cannot be used when only one type of image data is present.

The image processors 14 and 15 are provided with respect to the corresponding image data such that the ultrasonic image data and the X-ray image data are processed simultaneously.

Moreover, each of the data transmission lines for the ultrasonic image data and the X-ray image data has two bus lines so that the display device 8 can display the original image and a processed image (for example, the enlarged or reduced image) at the same time.

The ultrasonic image processor 14 and the X-ray image processor 15 achieve general image processing such as filtering, white-black reversal, recursive filtering for removing noise, rotation, and panning, etc.

Figure 3:
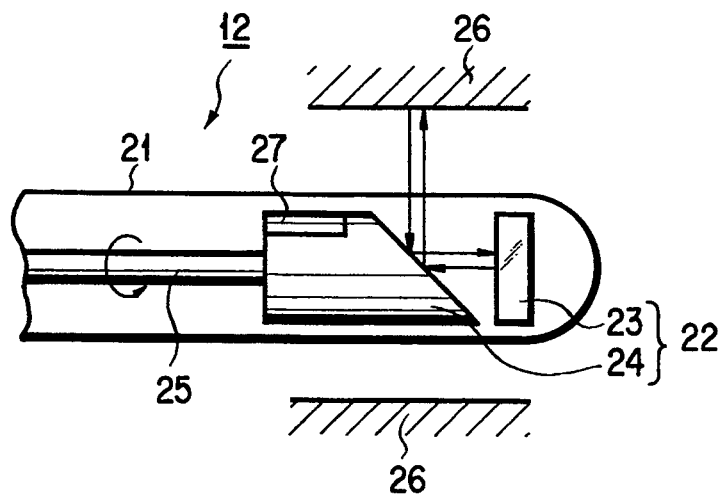
FIG. 3 shows an ultrasonic catheter of the first embodiment.

The ultrasonic catheter system 12, as shown in FIG. 3, includes an ultrasonic catheter 21 which is inserted into a blood vessel and an ultrasonic probe 22 which is arranged at the distal end of the ultrasonic catheter 21. The ultrasonic probe 22 includes an ultrasonic transducer 23 which transmits an ultrasonic wave in the direction of the axis of the catheter 21 and receives the reflected wave, and an ultrasonic mirror 24 whose reflecting surface is placed at an angle of 45° to the direction of the axis of the catheter. Thus, the ultrasonic wave transmitted from the ultrasonic transducer 23 in the direction perpendicular to the axis of the catheter. The ultrasonic mirror 24 is mounted to the axis 25 aligned with the axis of the catheter, is rotated together with the axis 25 by a driving source which is not shown. By this mechanism, the ultrasonic wave transmitted from the transducer 23 is radially scanned with the axis of the catheter as a central point, thereby achieving the radial scan of the whole circumference of the wall of the blood vessel under examination. As a result, as shown in FIG. 4, the ultrasonic tomogram appearing like a cross-section of a hollow tube of the 360° round wall of the blood vessel 26 with the distal end of the catheter 21 as a central point can be obtained.

To the distal end of the catheter 21, for example, to a portion of the ultrasonic mirror 24 is mounted a portion 27 which is impermeable to the X-rays (hereinafter referred to as an x-ray impermeable portion). As a result, when radiograph is taken by the X-ray TV system 10 while the ultrasonic catheter 21 is inserted in a blood vessel, the X-ray impermeable portion 27 appears as a black spot in the radiograph, thus helping to determine the position of the distal end of the ultrasonic catheter 21.

The system controller 4 can be switched from recording to reproducing and vice versa. In diagnosis, an important image is generally recorded and a decision of a disease is determined based on the reproduced image. A test image for finding a location of the catheter which is not important for diagnosis is not recorded. During recording, the system controller 4 transmits at least either of the X-ray image (including, the black dot representing the X-ray impermeable portion 27) obtained by the X-ray TV system 10 or the ultrasonic tomogram obtained by the ultrasonic catheter system 12, from the data acquisition system 6 to the data processing system 7. The data acquisition system 6 detects a time when the image is obtained together with the image, and stores it as attribute data of the image into the memory 13 together with the image data. During recording, the image data which has been delivered to the data processing system 7 is stored in the image memory 13, processed as needed by the ultrasonic image processor 14 and the X-ray image processor 15, and transferred to the image display 8.

The system controller 4 transmits at least either of the x-ray image data or the ultrasonic image data stored at the same time in the image memory 13, to the data processor 7.

The operation of the first embodiment having the structure as described above will be described below. At first, the ultrasonic catheter 21 is inserted into a blood vessel of the patient. As soon as the catheter 21 is inserted, the radiograph is taken with the X-ray TV system 10. Operations for the ultrasonic catheter system 12 and for the x-ray TV system 19 are easy because the control panel 5 is common to the two operations. As described above, to the distal end of the catheter 21 is arranged the X-ray impermeable portion 27, so that on the radiograph taken by the X-ray TV system 10 the X-ray impermeable portion appears as a black dot.

The X-ray image data is temporarily stored in the image memory 13 of the data processing system 7, and the X-ray image data delivered from the image memory 13 is transferred to the display device 8 as needed through the X-ray image processor 15.

When an X-ray image (live image) with the X-ray impermeable portion 27 displayed thereon is displayed on the display device 8, the system controller 4 may display the live image as being overlapped on the roadmap image.

For this purpose, after the ultrasonic catheter 21 having been inserted into a blood vessel near the region of interest (ROI), a contrast medium is injected through the opening (not shown in FIG. 3) at the distal end of the catheter 21, and the image of the blood vessel is taken by the X-ray TV system 10. This image is stored in the image memory 13 as a roadmap image. Then, when the X-ray image data of a live image is transferred to the data processing system 7, a synthesis image is formed by the roadmap image and the live image and is displayed on the display device 8. In the synthesis image, because the roadmap image indicating the shape of the blood vessel and the live image indicating the location of the X-ray impermeable portion 27 at the distal end of the catheter 21 appear as being overlapped with each other, the location of the distal end of the catheter 21 in the blood vessel can easily be determined. When the two images are made different from each other in density, they are easily distinguished.

As stated above, because the catheter 21 can be inserted while its location in the blood vessel is being checked through the radiograph, it can be guided safely to the ROI without giving undue pain to the patient.

When it is confirmed that the distal end of the catheter 21 reaches the ROI, the probe 22 is energized to emit an ultrasonic wave from the transducer 23 and rotate the ultrasonic mirror 24 for obtaining the ultrasonic tomogram of the wall of the blood vessel adjacent to the ROI.

The ultrasonic tomogram data output from the catheter system 12 is transferred to the data processing system 7 through the data acquisition system 6, and stored temporarily in the image memory 13. The ultrasonic tomogram data read out from the image memory 13 is transferred to the display device 8 as appropriate through the ultrasonic image processor 14.

Meanwhile the radiography by the X-ray TV system 10 is continued, and the X-ray image data is transferred to the data processing system 7 through the data acquisition system 6 and stored in the image memory 13 of the data processing system 7, together with the ultrasonic image data obtained at the same time.

Further, as stated above, the roadmap image may be displayed, after being overlapped on the corresponding X-ray image, as a synthesis image.

Of the radiograph, ultrasonic tomogram, their synthesis images, and other processed image, any one or any combination of two or more images can be freely chosen for display by the operation panel 5. The system controller 4 transfers the selected image data to the display device 8. Accordingly, the display device 8 can display only the synthesis image or ultrasonic image in a single frame, or it can display both synthesis and ultrasonic images in a multi-window mode.

Further, the ROI cursor can be applied to the synthesis and ultrasonic images, and the area selected by the ROI cursor can be enlarged and displayed in a third window.

When a plurality of image data are selected, those data are individually displayed in the display device 8 in a multi-window mode. The size and position of individual windows can be controlled with the joystick or the like mounted on the operation panel 5.

As described above, according to the first embodiment, a diagnostic apparatus for circulatory systems integrating diagnostic functions based on an ultrasonic tomogram imaging and a radiography is presented, and this helps not only to reduce the space for apparatus installment in the examination room, but also to simplify the procedures involved in diagnosis and therapy for circulatory organs.

In addition, because the position of the ultrasonic probe can be determined, the operator can not only insert the ultrasonic catheter safely but also know the exact position of the wall of the blood vessel in ultrasonic tomogram with respect to the patient's body regardless whether it is currently recorded in the memory or reproduced from the memory.

It is needless to say that the ultrasonic tomogram, the x-ray image indicating the location of the ultrasonic catheter, and their enlarged or reduced images respectively or in combination can be displayed, and any plurality of images can be displayed in one monitor.

Other embodiments according to the present invention will be described below. In the description of those embodiments, a portion which is common to the first embodiment will be omitted.

Second Embodiment

In the first embodiment, for determining the distal end location of the ultrasonic catheter 21 in the X-ray image, the X-ray image data with an indication of the X-ray impermeable portion 27 are stored in the image memory 13. By contrast, in a second embodiment, the X-ray image data is not stored in the image memory 13. Instead, the X-ray image processor 15 automatically detects the location of the X-ray impermeable portion 27 in the radiograph, and memorizes only this location data in the image memory 13. In particular, the system controller 4 transfers at least either the location data of the X-ray impermeable portion 27 obtained by the X-ray image processor 15 or the ultrasonic tomogram data obtained by the ultrasonic catheter 12, from the data acquisition system 6 to the data processing system 7. The image data transferred to the data processing system 7 is stored in the image memory 13, processed, when necessary, by the ultrasonic image processor 14 or the X-ray image processor 15, and transferred to the display device 8.

The system controller 4 transfers, during reproducing, either the location data or the ultrasonic tomogram data recorded at the same time with the image of interest stored in the image memory 13, to the display device 8.

In the first embodiment, the distal end location of the ultrasonic probe 21 or the location of the wall of the blood vessel under examination is identified by overlapping the X-ray image including a picture of the X-ray impermeable portion 27 as a black dot on the corresponding roadmap image, while in the second embodiment, the X-ray image is analyzed during recording, coordinate data regarding the location of the X-ray impermeable portion 27 is obtained, and a marker image indicating the location of the X-ray impermeable portion 27 is overlapped on the corresponding roadmap image, to identify the distal end location.

In particular, the system controller 4 analyzes the radiograph, identifies the distal end location of the x-ray impermeable portion 27, and displays it in the same coordinate system with the roadmap image. Then, the system controller 4 transfers this location coordinate data to the image memory 13 of the data processing system 7. The X-ray image processor 15 overlaps the image indicating the distal end location at the corresponding point of the roadmap image in the same coordinate system. This location mark image can take any form as long as it can be distinguished when it is overlapped on the roadmap image. The mark may take the same form as does the X-ray impermeable portion 27, or a simple form such as circle, triangle, etc.

The system controller 4 transfers this synthesis image comprising the marker image overlapped on the roadmap image to the display device 8. It should be noted here that because the location information and roadmap image are stored in the image memory 13, they can be read out from the image memory 13 and transferred to the display device 8 to reproduce the synthesis image, even after completion of diagnosis, as in the first embodiment.

According to the second embodiment, contrary to the first embodiment, it is not necessary to memorize the image having the X-ray impermeable portion 27 and only the coordinate data regarding the distal end location is memorized. Thus, it can spare a large capacity of the image memory 13.

As a means for detecting the coordinate of the distal end of the catheter 21, an explanation was given above in the sense that the X-ray impermeable portion 27 is provided in the catheter and the x-ray image having a picture of that part is analyzed. Other methods may be used. For example, a distortion gauge is placed in the catheter 21 along the axis thereof and the output signal from this distortion gauge is calculated to give the shape of the catheter 21, which serves for detection of the location of the ultrasonic probe.

Third Embodiment

Third embodiment relates not only to diagnosis but also to therapy. For this purpose, during recording, the system controller 4 transfers either the coordinate data of the X-ray impermeable portion 27 (first X-ray impermeable portion in the third embodiment) obtained from the X-ray image processor 15 or the ultrasonic tomogram obtained by the ultrasonic catheter 12, from the data acquisition system 6 to the data processing system 7. While the therapeutic catheter is inserted, the system controller 4 transfers either the coordinate data of an X-ray impermeable portion (second X-ray impermeable portion) which is arranged adjacent to the distal end of the therapeutic catheter or the ultrasonic image approximately corresponding with this second coordinate data, which is reproduced from the data acquisition system 6 to the data processing system 7.

During examination of circulatory systems, it often occurs that after the wall of the blood vessel is observed by the use of the ultrasonic catheter 21, the stenotic part of the blood vessel is expanded utilizing a therapeutic catheter such as a balloon catheter, etc. For such therapy it will be greatly helpful if, in addition to the information regarding the location of the therapeutic catheter, the ultrasonic tomogram of the affected vessel is given.

At first, as in the first or second embodiment, the ultrasonic tomogram and the X-ray image are obtained during the insertion of the ultrasonic catheter 21 and the ultrasonic image of the wall of the blood vessel and the coordinate data indicating the location of the first X-ray impermeable portion are stored in the image memory 13.

Then, the therapeutic catheter is inserted. This therapeutic catheter, like the ultrasonic catheter 21, is equipped with an X-ray impermeable portion (the X-ray impermeable portion provided in the ultrasonic catheter 21 is numbered first and that provided in the therapeutic catheter, second). Radiography is performed, and the location of the second X-ray impermeable portion is detected by the X-ray image processor 15. When the distal end location of the therapeutic catheter is identified, the ultrasonic tomogram containing the same coordinate data (regarding the first X-ray impermeable portion) is retrieved from the image memory 13. In other words, the ultrasonic tomogram indicating the distal end location of the therapeutic catheter is searched among the images stored in the memory 13.

When together with this ultrasonic tomogram, a synthesis image comprising the marking image indicating the location of the therapeutic catheter overlapped on the roadmap image is displayed, it will be possible to treat the wall of the blood vessel while monitoring its state, so that proper treatment is ensured. Wrong intervention to unaffected parts can be avoided.

Further, if, together with the ultrasonic tomogram indicating the current distal end location, those proceeding and succeeding it are displayed, the wall of the blood vessel looks as if the visual point is placed within the blood vessel and thus the treatment of the vessel is facilitated. In this case, it is necessary to modify the tone or gradation of the images so as to give a perspective. Further, it is desirable to display the ultrasonic tomogram of the current distal end location and those preceding and succeeding it in a three dimensional manner.

According to the third embodiment, it is possible to make therapy, during the usage of a therapeutic catheter, while retrieving the ultrasonic image corresponding with the current location of the therapeutic catheter, and monitoring the image on display.

Fourth Embodiment

FIG. 5 shows the structure of the ultrasonic catheter 12 according to the fourth embodiment, which is similar to that of the first, second, or third embodiment but additionally comprises a rotational timing detection circuit 53. Further, whereas the X-ray impermeable portion 27 in the first, second, or third embodiment is provided to detect the distal end of the catheter, an X-ray impermeable portion 52 in the fourth embodiment is provided for detecting the rotational position of the ultrasonic mirror 24 with respect to the radiation direction of the X-ray by inspecting the x-ray image. The X-ray impermeable portion 52 must have such a shape as to permit the detection of the radiation direction of the X-ray based on at least one of the X-ray images obtained during one rotation (360°) of the ultrasonic mirror 24.

Figure 6:
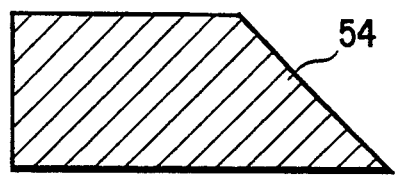
FIG. 6 shows an X-ray impermeable portion for rotational timing detection in the fourth embodiment.

For example, if the ultrasonic mirror 24 having shape of a cylinder cut obliquely at the end is taken as a whole as the X-ray impermeable portion 54, and if its x-ray image has a shape as illustrated in FIG. 6, it can be detected that the mirror 24 is exposed to the X-ray radiated in the direction parallel to the reflection surface of the ultrasonic mirror 24, or, perpendicular to the paper surface of FIG. 6.

Figure 7A:
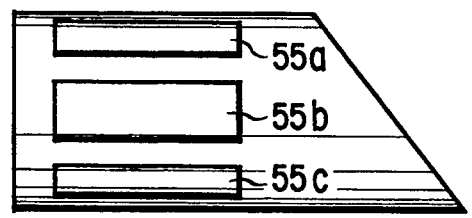
FIGS. 7A, 7B, and 7C show other examples of the X-ray impermeable portion in the fourth embodiment.
Figure 7B:
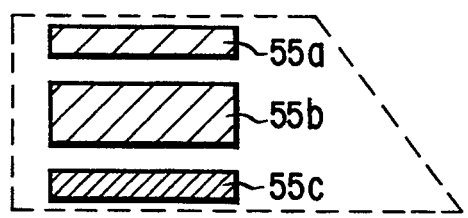
Figure 7C:
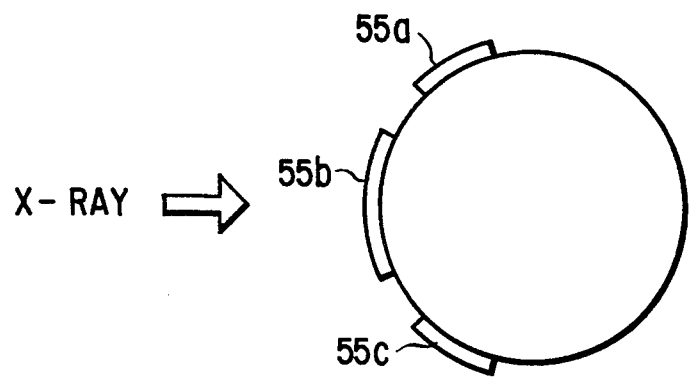

Further, as shown in FIG. 7A, if the X-ray impermeable portion is assumed as comprised of three X-ray impermeable strips 55a, 55b, and 55c each having the same area but different transmission (their transmission decreases in order of 55a, 55b, and 55c) which have been attached to the cylindrical surface of the ultrasonic mirror 24, and their images are recognized to be roughly as represented in FIG. 7B, it can be determined that the X-ray is radiated in the direction as indicated in FIG. 7C.

Figure 8:
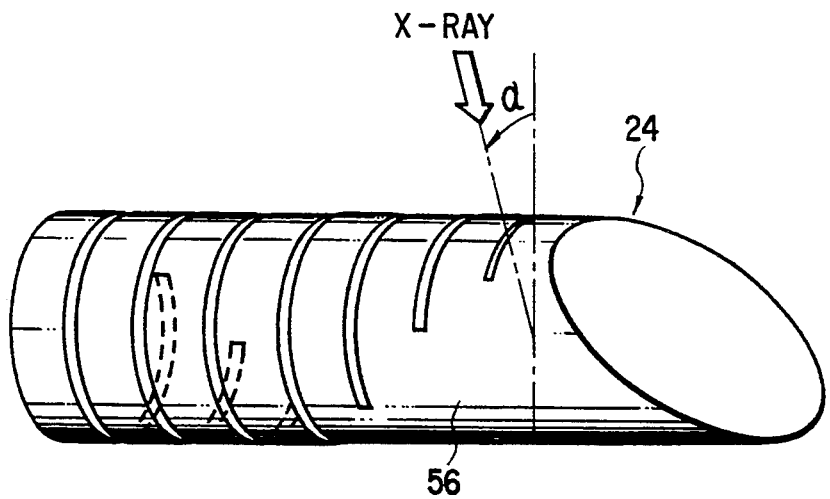
FIG. 8 shows a further example of the x-ray impermeable portion in the fourth embodiment.
Figure 9A:
FIGS. 9A–H illustrate the principle for detecting rotational timing using the X-ray impermeable portion shown in FIG. 8.
Figure 9B:
Figure 9C:
Figure 9D:
Figure 9E:
Figure 9F:
Figure 9G:
Figure 9H:
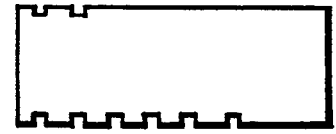

Furthermore, as shown in FIG. 8, the ultrasonic mirror 24 is made of an X-ray impermeable material and has 7 grooves which have unequal lengths and are cut around its outer surface, and this may be taken as the X-ray impermeable portion 56. When in FIG. 8, the radiation angle $\alpha$ is changed from 0° through 45°, 90°, 135°, 180°, 225° and 270° to 315°, the corresponding X-ray image of the X-ray impermeable portion 56 are illustrated in (a) to (h) of FIG. 9. For example, if a given X-ray image of the X-ray impermeable portion 56 is recognized as equal to (a) in FIG. 9, the radiation angle $\alpha$ in FIG. 8 is 0° or the X-ray comes from angle 0°.

With the X-ray impermeable portion 56 as described above, its X-ray image changes in accordance with the radiation direction of the X-ray as shown in FIG. 9, so that it is possible to distinguish more minutely the rotation angles of the ultrasonic mirror 24.

The detection of the radiation direction based on the image of the X-ray impermeable portion 54, 55, or 56 may be achieved with naked eyes, or by an automatic sensor. When this is done with naked eyes, an image processing such as enlarging may be used as appropriate.

The rotational timing detection circuit 53 is interlocked via the shaft 25 with the driving mechanism (not shown in FIG. 5) for driving the ultrasonic mirror 24, and the assembly is so constructed as to give the rotational timing signal such as a pulse when the ultrasonic mirror 24 rotates to a given angular position.

The procedures for generating a rotational timing detection signal using the X-ray impermeable portion 54, 55, or 56 will be given below. At first, the ultrasonic mirror 24 is manually rotated to a desired rotational angle, and the reference direction of the ultrasonic mirror 24, for example, the direction as viewed from which the area of the reflecting surface of the mirror is the maximum, is aligned with the radiation direction.

Whether they are aligned with each other is checked by monitoring the corresponding X-ray image of the X-ray impermeable portion 54, 55, or 56. The rotational timing detection circuit 53 is reset at this rotational position. The rotational timing detection circuit 53 is formed of an initial angle memory for storing the reset rotational angle as an initial angle and a comparator for comparing the rotational angle signal output from the driving mechanism and the initial angle. Therefore, the rotational timing detection circuit 53 can deliver a pulse as the rotational timing detection signal whenever the reflecting surface of the ultrasonic mirror 24 directs itself towards the X-ray radiation direction.

Figure 10A:
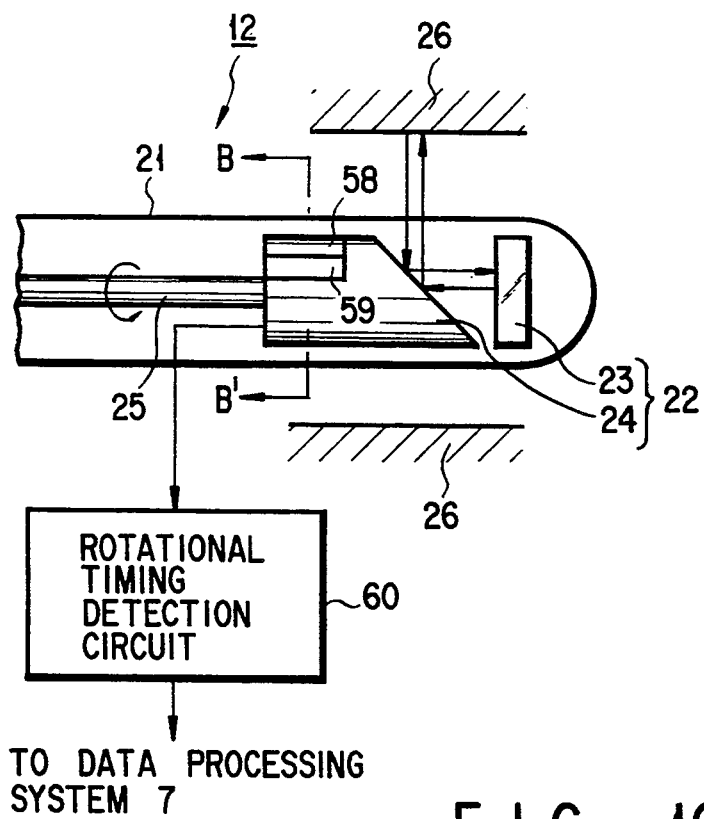
FIGS. 10A and 10B show further examples of rotational timing detection in the fourth embodiment.
Figure 10B:
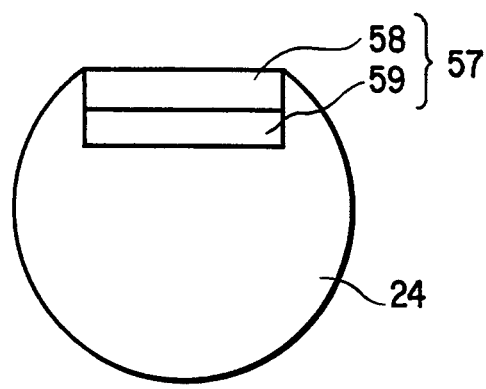
Figure 11A:
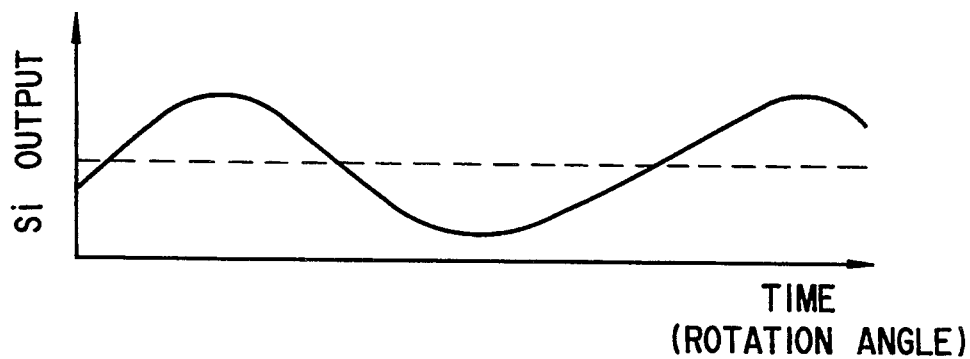
FIGS. 11A, 11B, and 11C illustrate the manner in which an offset angle is detected in the fourth embodiment.

The above rotational timing detection circuit 53 may erroneously detect the timing if the rotation of the driving mechanism cannot be equal to the rotation of the mirror 24 due to the distortion of the shaft 25. In order to overcome this problem, the rotational timing detection circuit may be formed of a detection means 57 placed close to the probe 22, and a rotational timing detection circuit 60 which delivers a rotational timing signal using the output from the detection means 57. The lateral cross-sectional view of the detection means 57 is shown in FIG. 10A, and the enlarged cross-sectional view along the line B—B', in FIG. 10B. The detection means 57 is formed of, as shown in FIG. 10B, a scintillator 58 and an Si sensor 59 which generates an electric signal in accordance with the intensity of the X-ray detected. Accordingly, when the ultrasonic mirror 24 rotates at a constant speed, the wave of the electric signal delivered from the Si sensor 59 has an approximately sinusoid curve as shown in FIG. 11A, and it takes a maximum when the ultrasonic mirror 24 is so rotated as to make the detection means 57 (its surface) opposite the X-ray radiation direction while, when the ultrasonic mirror 24 so rotates as to make the detection means 57 (its back surface) opposite the X-ray radiation direction, it takes a minimum.

Figure 11B:
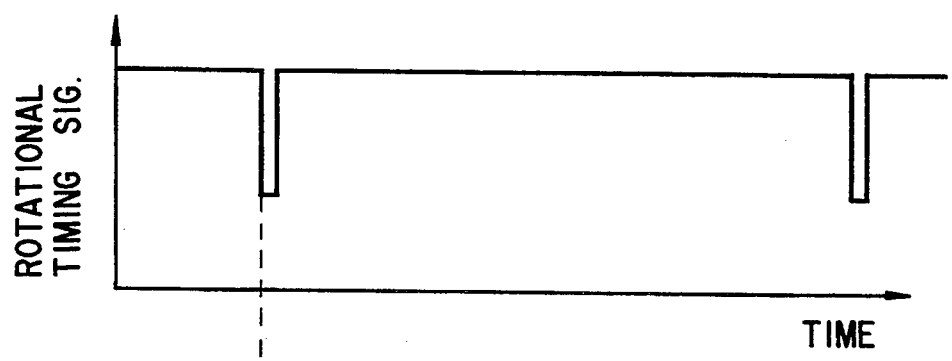

The rotational timing detection circuit 60 detects the positive peak of the input signal, and delivers a pulse as the rotational timing detection signal each time such peak is detected (FIG. 11B). For facilitating the detection of peaks by enlarging the difference between maximum and minimum, an X-ray impermeable portion such as lead may be placed below the Si detection means 59. As is evident from above, the rotational timing detection circuit 60 can deliver a pulse as the rotational timing detection signal each time the ultrasonic mirror 24 is so rotated as to make the detection means 57 (its surface) opposite the X-ray radiation direction.

Next, description will be given of the means by which to find an offset angle from the rotational timing signal delivered from the rotational timing detection circuit 53 or 60. The data processing system 7 comprises an r-$\theta$ address correction circuit 71 which allows the radiation direction to take a given constant direction in the ultrasonic tomogram on the display device 8, by calculating the offset angle from the rotational timing detection signal and a VD signal (synchronizing signal), and by modifying the r-$\theta$ address of the ultrasonic tomogram in accordance with the calculated offset angle. The r-$\theta$ address is the address information the ultrasonic tomogram conveys, and r is the distance from the ultrasonic catheter 21 and the pixel reflecting the ultrasonic wave and $\theta$ is the rotational angle ($\alpha$) of the ultrasonic mirror 24.

Figure 12:
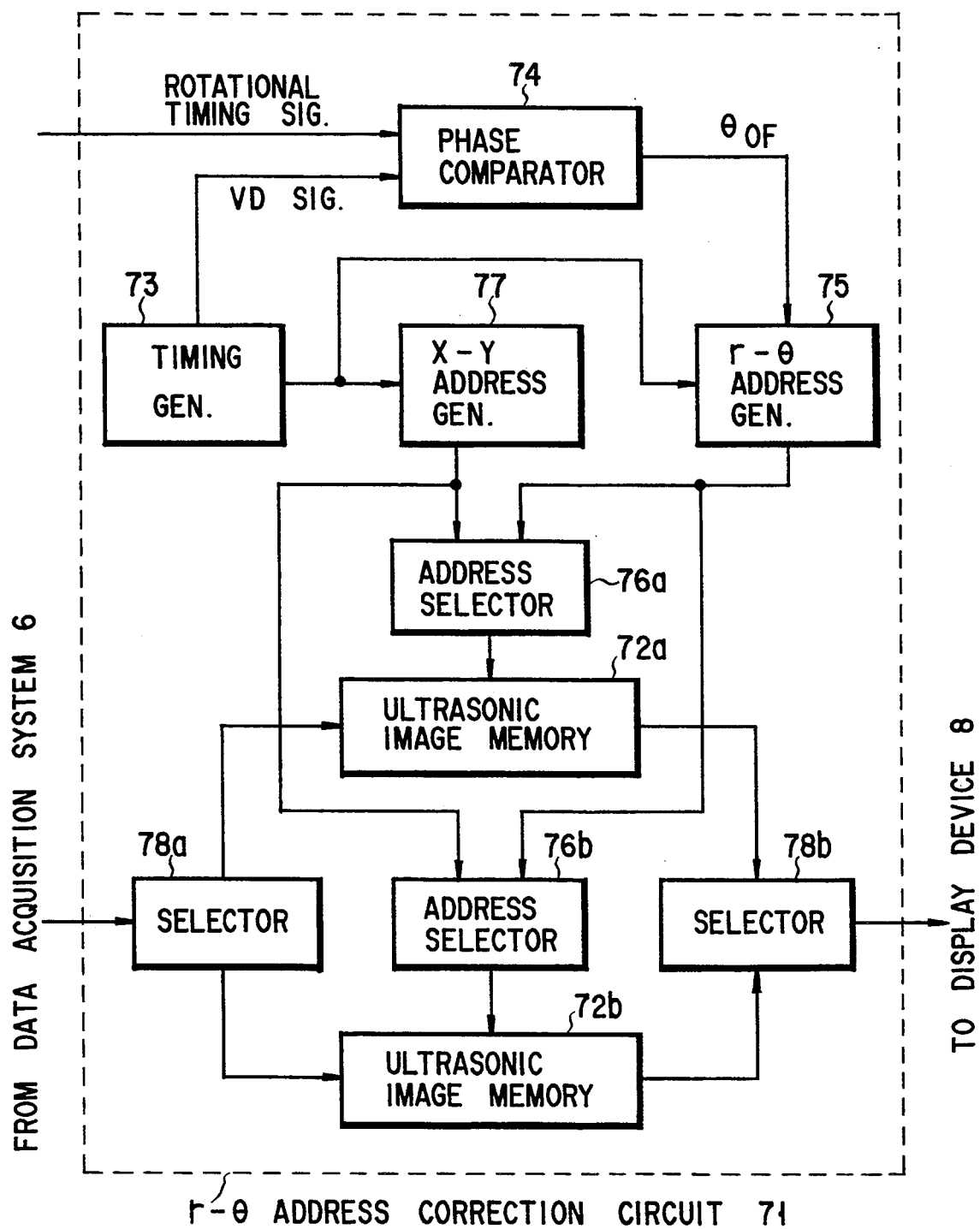
FIG. 12 is a block diagram illustrating an example of an $r$-$\theta$ address correction circuit in the fourth embodiment.

The block diagram of the r-$\theta$ address correction circuit 71 is shown in FIG. 12. This correction circuit 71 comprises ultrasonic image memories 72a and 72b which store the ultrasonic image data from the data acquisition system 6, a timing generating circuit 73 which generates the VD signal which corresponds to the frame period of the display device 8, a phase comparator 74 which detects the phase difference between the rotational timing detection signal which is supplied from the rotational timing detection circuit 53 or 60 through the data acquisition system 6 and the VD signal and delivers the difference as the offset angle $\theta_{OF}$, an r-$\theta$ address generating circuit 75 for generating the r-$\theta$ address which is modified in accordance with the VD signal and the offset angle $\theta_{OF}$, an X-Y address generating circuit 77 for generating the X-Y address based on the VD signal, address selectors 76a and 76b for determining the address of the memories 72a and 72b in accordance with the r-$\theta$ address or X-Y address, and selectors 78a and 78b which exchange the stored area or read-out area for the ultrasonic image between memories 72a and 72b.

Figure 11C:
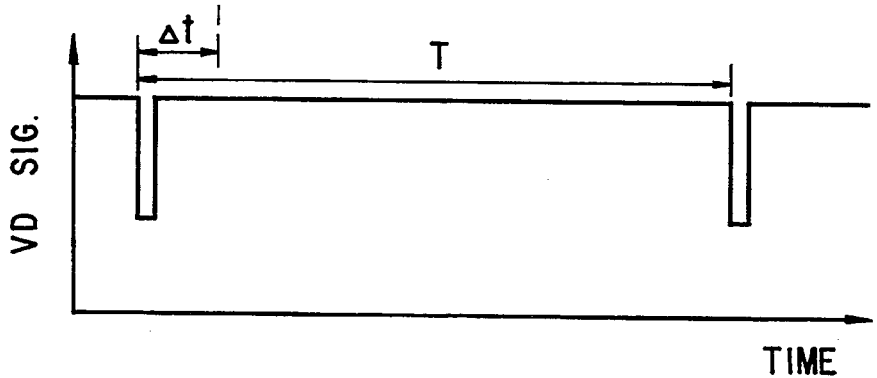

When the rotational timing detection signal as illustrated in FIG. 11B is fed into the r-$\theta$ address correction circuit 71, the phase comparator 74 compares the rotational timing detection signal and the VD signal as illustrated in FIG. 11C and output from the timing generating circuit 73, and detects their phase difference $\Delta t$. Because the timing generating circuit 73 does not generate the VD signal in synchronism with the rotation of the ultrasonic mirror 24, normally a phase difference exists between the rotational timing detection signal and the VD signal.

The phase comparator 72, using the $\Delta t$ and a period T, calculates the offset angle $\theta_{OF}$ as defined below. Namely, the offset angle is the difference in angle between the reference angle of the radial scanning ($\theta=0$ or X-ray radiation direction) and the reference direction (for example, upward) of the image on the display.

$$\theta_{OF} = -2\pi \Delta t / T$$

Because the rotation frequency of the ultrasonic mirror 24 is made roughly equal to the frame frequency of the display, the display device 8 displays one ultrasonic tomogram obtained by one rotation of the ultrasonic mirror 24 per one frame period. Accordingly, when the phase is coincident between the VD signal and the rotational timing detection signal, or, the offset angle $\theta_{OF}$ is 0, as shown in FIG. 13A, a given direction in display, e.g., upward direction constantly points to the X-ray radiation direction.

However, if an offset angle $\theta_{OF}$ is present as a result of distortion or rotation of the catheter 21, and the relevant image is displayed with the r-$\theta$ address being left uncorrected, the ultrasonic tomogram is displayed being displaced by that offset angle $\theta_{OF}$, as shown in FIG. 13B.

In order to prevent this displacement of the image, the $\theta$ address is shifted by the offset angle $\theta_{OF}$ in the opposite direction of the offset. As a result, it is possible to maintain the X-ray radiation direction constantly upward, as shown in FIG. 13C.

When a wall of the blood vessel is displayed as an image on the display device 8, it is desirable to take as a reference not the X-ray radiation direction but the vertical direction of the ultrasonic tomogram. In that case, if the X-ray radiation direction is fixed to be coincident with the vertical direction, the above r-$\theta$ address correction circuit 71 applies unaltered. However, if the X-ray radiation direction can be altered by rotating the X-ray tube holding arm (not shown in the figure) attached to the X-ray TV system 10, the arm angle $\theta_A$ is fed into the r-$\theta$ address generating circuit 75 and the address in the direction of $\theta$ should be corrected based on the offset angle $\theta_{OF}$ and the arm angle $\theta_A$.

Further, the data processing system 7 may include an r-$\theta$ address correction circuit 81 which is so constructed as to allow, by calculating the offset angle from the rotational timing detection signal and the VD signal and correcting the r-$\theta$ address of the image which marks the x-ray radiation direction based on the offset angle, that X-ray radiation direction marking image to be displayed together with the ultrasonic tomogram on the display device 8.

Figure 14:
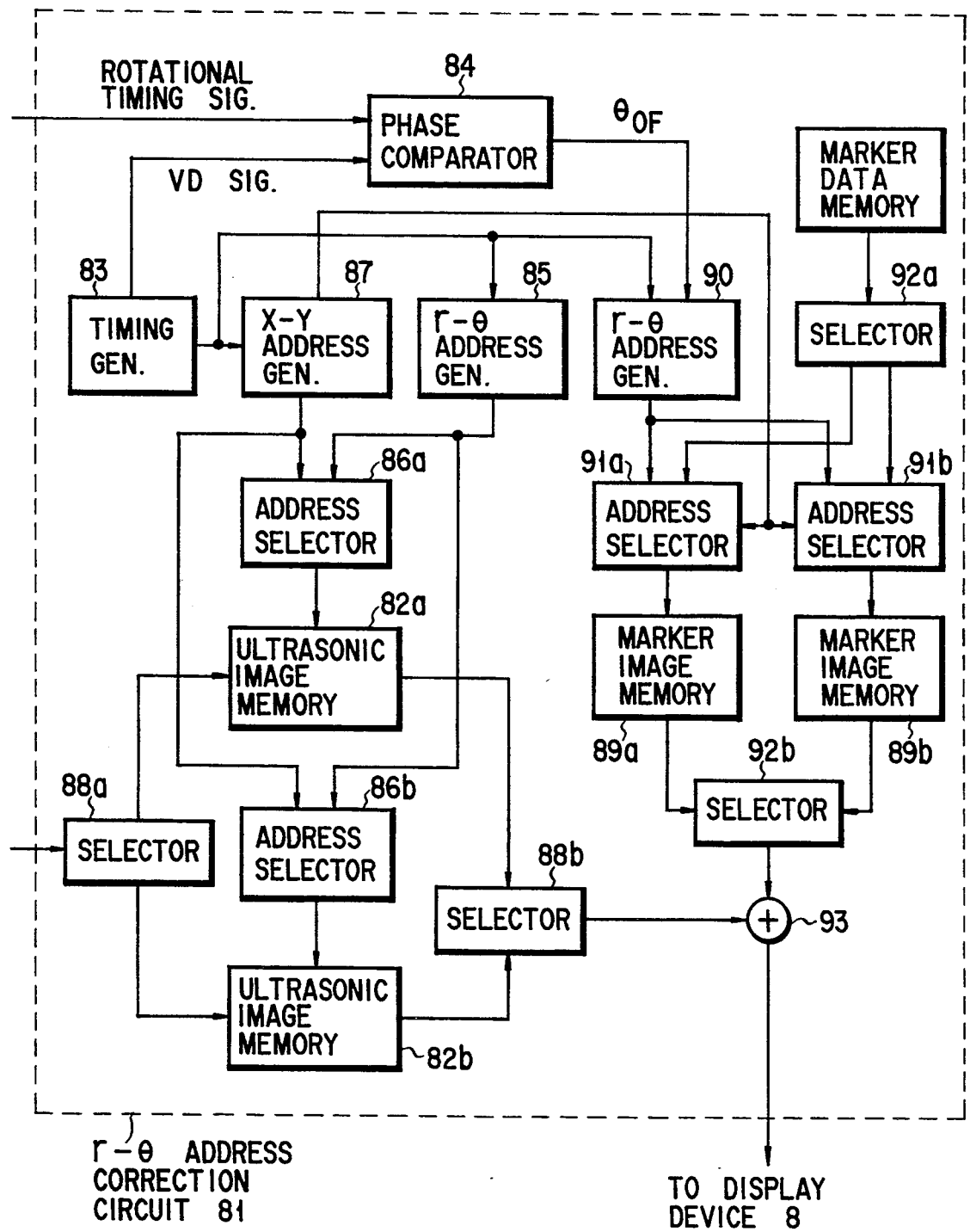
FIG. 14 is a block diagram illustrating another example of the $r$-$\theta$ address correction circuit in the fourth embodiment.

The block diagram of this correction circuit 81 is shown in FIG. 14. This circuit includes memories 82a and 82b which store the ultrasonic image data supplied from the data acquisition system 6, a timing generating circuit 83 which generates the VD signal, a phase comparator 84 which detects the phase difference between the rotational timing detection signal which is delivered from the rotational timing detection circuit 53 or 60 and the VD signal, and delivers the difference as the offset angle $\theta_{OF}$, an r-$\theta$ address generating circuit 85 which generates the r-$\theta$ address of the ultrasonic image, marker image memories 89a and 89b which store the marker image data indicating the X-ray radiation direction, an r-$\theta$ address generating circuit 90 which generates the corrected r-$\theta$ address for the marker image data based on the VD signal and the offset signal $\theta_{OF}$ delivered from the phase comparator 84, an X-Y address generating circuit 87 which generates the X-Y address from the VD signal, address selectors 86a and 86b; 91a and 91b which determine the address of the ultrasonic image memories 82a and 82b and the address of the marker image memories 89a and 89b in accordance with the r-$\theta$ address and X-Y address, selectors 88a and 88b; 92a and 92b which exchange the stored area for the ultrasonic image between the ultrasonic image memories 82a and 82b and the read-out area for the marker image between the marker image memories 89a and 89b, a mixer 93 which synthesizes the ultrasonic image and the marker image, and a memory 94 which stores the marker data.

This r-$\theta$ address correction circuit 81 is approximately the same as the r-$\theta$ address correction circuit 71 shown in FIG. 12, but, instead of correcting the r-$\theta$ address of the ultrasonic image, it corrects the r-$\theta$ address of the marker image indicating the X-ray radiation direction. To be more specific, although the X-ray radiation direction changes in the screen of the display device 8, such change is recognized by referring to the marker image which is also changed in the screen, so that it is possible to know from what direction of the wall of the blood vessel the X-rays are radiated.

According to the fourth embodiment, the system controller 4, during recording, transfers either the ultrasonic tomogram of the wall of the blood vessel obtained by the ultrasonic catheter system 12 or the offset angle detected by the rotational timing detection circuit 53, to the display device 8 through the data processing system 7, and during reproduction, transfers either the ultrasonic image data obtained at the same time and stored in the data processing system 7 or the offset angle, to the display device 8.

According to the fourth embodiment, for example, the ultrasonic tomogram can be displayed such that the wall of the blood vessel facing the patient's back (when the patient lies on bed, the wall of the blood vessel faces downward vertically) is always displayed downward, thus allowing one to easily know the location of the stenotic portion of the blood vessel with respect to the patient's body.

Fifth Embodiment

An ultrasonic catheter 101 according to a fifth embodiment, as shown in FIG. 15A, is so constructed that the angle $\alpha$ of the reflective surface of an ultrasonic mirror 24e can be altered from outside. This arrangement allows transmission of the ultrasonic wave against blood flow, thus enabling the measurement of the flow rate of the blood based on the Doppler effect of the ultrasonic wave. However, for determining the absolute value of the flow rate, it is necessary to know the angle $\alpha$.

For diagnosis of circulatory organs, after the wall of the blood vessel having been examined with the ultrasonic catheter 21, on occasion the flow rate of blood is measured. In this case, it will be greatly beneficial for therapeutic purposes if the distal end location of the catheter for measuring the flow rate of blood can be monitored from outside and the state of the wall of the blood vessel at the same location be displayed. In the fifth embodiment, as in the second embodiment, during the insertion of the ultrasonic catheter 21, the ultrasonic tomogram data and the information regarding the location of the wall of the blood vessel on the corresponding roadmap image at which the ultrasonic tomogram is obtained are stored in the memory 13.

Then, the catheter 101 for measuring the flow rate is inserted. The catheter 101 is equipped with a second X-ray impermeable portion 27e like the X-ray impermeable portion 27 for the ultrasonic catheter 21, so that the location of the second X-ray impermeable portion 27a can be detected by analyzing the X-ray image. The ultrasonic tomogram of the wall of the blood vessel that gives the same coordinate data with that supplied by the second X-ray impermeable portion 27e, is retrieved from the image memory 13. Thus, the current position of the blood flow measuring catheter 101 is checked by the X-ray TV system 10 and the ultrasonic tomogram data giving the same location is retrieved from the memory 13.

If, together with the ultrasonic image, the synthesis image where the image marking the location of the flow rate measuring catheter is overlapped on the roadmap image, is displayed on the display device 8, it is possible to measure the flow rate while monitoring the state of the wall of the blood vessel. The flow rate thus obtained, the reflection index, and the reflection surface angle $\alpha$ can be displayed overlapped on this synthesis image or the ultrasonic image.

The system controller 4, during insertion of the flow rate measuring catheter, is so operated that at least either the second ultrasonic image approximately corresponding with the second coordinate data, the second synthesis image which overlaps the mark indicating the location of the second X-ray impermeable portion 27e on the roadmap image based on the second coordinate data, or the enlarged or reduced second synthesis image or the second ultrasonic image, is transferred to the display device 8. Thus, the measurement data obtained by the catheter can be synthesized into either the second ultrasonic image or second synthesis image.

Therefore, as shown in FIG. 15B, a vector display indicating the angle $\alpha$ or a numerical value indicating the flow rate can be overlapped on the marker image indicating the position of the blood flow measurement catheter displayed on the roadmap image.

Further, like the previous embodiments, the system controller 4 is so constructed as to allow 2 or more image data transferred to the display device 8 to be displayed at any size and position as appropriate in a multi-window mode.

According to the fifth embodiment, the system controller 4 is so constructed as to, during recording, transfer at least either the ultrasonic tomogram of the wall of the blood vessel obtained by the ultrasonic probe 22 or the coordinate data obtained from the X-ray image of the first X-ray impermeable portion 27, to the display device for display through the data processing system 7, and, during insertion of the flow rate assay catheter 101, to transfer at least either the second coordinate data obtained from the X-ray image of the second x-ray impermeable portion 27e, the ultrasonic image corresponding with the second coordinate data, or the measurement data obtained by the catheter 101, to the display device 8 through the data processing system 7.

According to the fifth embodiment, during the usage of the flow rate measuring catheter 101, the previously recorded ultrasonic image corresponding with the location of the flow rate measuring catheter is retrieved to be displayed, and, it is possible, while monitoring this ultrasonic image, to measure the flow rate with the flow rate measuring catheter.

Sixth Embodiment

A sixth embodiment is an improvement of the display of the ultrasonic tomogram. During recording, as in the previous embodiments, at first, the roadmap is obtained and is stored in the image memory. When the ultrasonic catheter 21 is inserted into the blood vessel, the ultrasonic tomogram and the X-ray radiograph are simultaneously obtained. The ultrasonic tomogram is stored in the image memory together with the coordinate data of the distal end of the catheter at which the ultrasonic tomogram is obtained. During reproducing, the ultrasonic tomogram 100 is retrieved from the image memory and is displayed on a central portion of the display. The roadmap image 102 is also retrieved from the image memory and is displayed on a peripheral portion of the display in a smaller size than the ultrasonic tomogram 100. In the roadmap image 102, the marker image 104 of the distal end of the catheter is displayed at the position corresponding to the location information of the distal end of the catheter at which the ultrasonic tomogram 100 is obtained.

According to the sixth embodiment, the ultrasonic tomogram 100 of the wall of the blood vessel can be monitored while monitoring the position of the wall in the roadmap image 102. Therefore, proper diagnosis is ensured.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the ultrasonic tomogram can be derived not through radial scan but through sector scan below 360° or less, or through linear scan. Further, the X-ray impermeable portion can be spared, and instead, at least a part of the mirror or catheter may be composed of a certain x-ray impermeable material such as lead.

According to the present invention, there is provided a diagnostic apparatus for circulatory systems in which the X-ray radiation direction in the ultrasonic tomogram is always displayed at a constant angle with respect to the patient's body, and the ultrasonic tomogram and the X-ray image are displayed side by side. Therefore, the location and orientation of the ultrasonic tomogram relative to the patient can be accurately identified.

Moreover, the apparatus combines the functions for ultrasonic diagnosis and X-ray diagnosis into a coherent system, thereby allowing the apparatus installment space to be reduced and the operability to be improved.

What is claimed is:

1. A diagnostic apparatus for diagnosing the circulatory system of a patient, comprising:

x-ray diagnostic means for irradiating a portion of the patient's body with X-rays to obtain a radiograph of said portion of the patient's body;

ultrasonic diagnostic means, for insertion into the circulatory system of the patient, for scanning a circulatory organ with an ultrasonic wave to thereby obtain an ultrasonic tomogram;

control means, commonly connected to said X-ray diagnostic means and said ultrasonic diagnostic means, for controlling said X-ray diagnostic means and said ultrasonic diagnostic means;

signal processing means, commonly connected to said X-ray diagnostic means and said ultrasonic diagnostic means, for signal-processing the radiograph and the tomogram; and display means, commonly connected to said signal processing means, for displaying the radiograph and the ultrasonic tomogram, whereby said control means, said signal processing means and said display means are shared by said X-ray diagnostic means and said ultrasonic diagnostic means.

2. An apparatus according to claim 1, wherein said ultrasonic diagnostic means comprises:

a catheter to be inserted into a blood vessel of the patient;

an ultrasonic probe, arranged within said catheter, for transmitting the ultrasonic wave in a radial direction with an axis of the catheter as a central point, and receiving the ultrasonic wave reflected from the wall of the blood vessel, to obtain the ultrasonic tomogram of the wall of the blood vessel; and an X-ray impermeable portion arranged at a distal end of the catheter.

3. An apparatus according to claim 2, wherein said ultrasonic diagnostic means further comprises contrast medium injection means arranged at the distal end of the catheter.

4. An apparatus according to claim 3, wherein said ultrasonic X-ray diagnostic means comprises:

means for obtaining the radiograph prior to obtaining the ultrasonic tomogram while a contrast medium is injected into the blood vessel by said contrast medium injection means, and obtaining a roadmap image of the blood vessel;

means for obtaining the radiograph during obtaining of the ultrasonic tomogram, the radiograph including a picture of the X-ray impermeable portion indicating the distal end of the catheter; and means for displaying the radiograph in an overlapping relationship with respect to said roadmap image.

5. An apparatus according to claim 3, wherein said ultrasonic X-ray diagnostic means comprises:

means for obtaining the radiograph prior to obtaining the ultrasonic tomogram while a contrast medium is injected into the blood vessel by said contrast medium injection means, and providing a roadmap image of the blood vessel;

means for obtaining the radiograph while the ultrasonic tomogram is being obtained, and providing the radiograph including a picture of the X-ray impermeable portion indicating the distal end of the catheter;

means for detecting a location of the picture of the X-ray impermeable portion in said radiograph; and means for displaying a marker indicating the location of the catheter distal end according to the location detected by said detecting means in an overlapping relationship with respect to said roadmap image.

6. An apparatus according to claim 2, wherein said ultrasonic diagnostic means comprises:

means for rotating said ultrasonic probe with the direction of the axis of the catheter as a center;

means for storing an initial rotation position of said ultrasonic probe and delivering a rotational timing detection signal when the probe reaches the initial rotation position during rotation; and means for detecting a direction of the ultrasonic tomogram with respect to an X-ray radiation direction by detecting the phase difference between said rotational timing detection signal and a frame synchronization signal of the display device, and wherein said display means displays the ultrasonic tomogram such that the X-ray radiation direction in the ultrasonic tomogram maintains a predetermined direction.

7. An apparatus according to claim 2, wherein said ultrasonic diagnostic means comprises:

means for rotating said ultrasonic probe with the direction of the axis of the catheter as a center;

means for storing an initial rotation position of said ultrasonic probe and delivering a rotational timing detection signal when the probe reaches the initial rotation position during rotation; and means for detecting a direction of the ultrasonic tomogram with respect to an X-ray radiation direction by detecting the phase difference between said rotational timing detection signal and a frame synchronization signal of the display device, and wherein said display means displays a marker image for indicating an X-ray radiation direction on the ultrasonic tomogram.

8. An apparatus according to claim 1, wherein said display means further comprises means for displaying the radiograph and the ultrasonic tomogram taken at the same time in a multi-window manner.

9. A diagnostic apparatus for diagnosing the circulatory system of a patient, comprising:

ultrasonic diagnostic means, for insertion into the circulatory system of the patient, for scanning an ultrasonic wave and obtaining an ultrasonic tomogram, the ultrasonic diagnostic means including a first X-ray impermeable portion;

first X-ray diagnostic means for irradiating a portion of the patient's body with X-rays while said ultrasonic diagnostic means is inserted into the circulatory system of the patient, obtaining a radiograph of said portion of the patient's body including a picture image of the first X-ray impermeable portion, and detecting the location of the first X-ray impermeable portion from the radiograph;

means for storing, when said ultrasonic diagnostic means obtains the ultrasonic tomogram, the location of said first X-ray impermeable portion and the tomogram;

a catheter for insertion into the circulatory system of the patient, for therapy or measurement of a blood flow rate, the catheter including a second X-ray impermeable portion;

second X-ray diagnostic means for irradiating, when said catheter is inserted into the circulatory system of the patient, X-rays onto said portion of the patient's body, obtaining a radiograph containing a picture image of the second X-ray impermeable portion, and detecting a location of the second X-ray impermeable portion from the radiograph; and means for retrieving, from said storing means, an ultrasonic tomogram obtained at a location of the first X-ray impermeable portion corresponding to the location of the second X-ray impermeable portion detected by said second X-ray diagnostic means, to thereby display the ultrasonic tomogram.

10. An apparatus according to claim 9, wherein said display means further retrieves, from said storing means, a first ultrasonic tomogram obtained at a location of the first X-ray impermeable portion which is preceding to the location of the second X-ray impermeable portion detected by said second X-ray diagnostic means and a second ultrasonic tomogram obtained at a location of the first X-ray impermeable portion which is succeeding to the location of the second X-ray impermeable portion detected by said second X-ray diagnostic means.

11. An apparatus according to claim 9, further comprising:

means for injecting a contrast medium into a blood vessel of the object;

means for producing a roadmap image of the blood vessel by obtaining a radiograph while a contrast medium is injected prior to obtaining the ultrasonic tomogram; and means for displaying a marker image indicating a location of a distal end of the catheter in an overlapping relationship with respect to the roadmap image at the location of the first X-ray impermeable portion.

* * * * *